United States Patent [19]

Galbraith et al.

[11] Patent Number: 4,597,665
[45] Date of Patent: Jul. 1, 1986

[54] DUAL COLLECTOR OPTICAL FLAW DETECTOR

[75] Inventors: Lee K. Galbraith, Mountain View; Karel Urbanek, Atherton, both of Calif.

[73] Assignee: Tencor Instruments, Mountain View, Calif.

[21] Appl. No.: 610,101

[22] Filed: May 14, 1984

Related U.S. Application Data

[63] Continuation-in-part of Ser. No. 559,909, Dec. 9, 1983.

[51] Int. Cl.$^4$ ............................................. G01N 21/00
[52] U.S. Cl. .................................. 356/237; 356/239; 356/431; 356/446; 250/563; 250/572
[58] Field of Search ............... 250/562, 563, 571, 572; 356/237, 239, 430, 431, 446

[56] References Cited

U.S. PATENT DOCUMENTS

| 3,663,824 | 5/1972 | Blaisdell et al. | 250/219 R |
|---|---|---|---|
| 4,243,891 | 1/1981 | Dobler et al. | 356/237 |
| 4,360,275 | 11/1982 | Louderback | 356/446 |
| 4,378,159 | 3/1983 | Galbraith | 356/237 |
| 4,380,032 | 5/1983 | Pfost | 356/237 |

*Primary Examiner*—John E. Kittle
*Attorney, Agent, or Firm*—Thomas Schneck

[57] ABSTRACT

A flaw detector for optically transmissive surfaces having a first light collector above the surface and a second light collector below the surface. A scanning light beam is directed into the first light collector through a beam entrance aperture and only light scattered from the surface is collected. Light specularly reflected from the surface exits the collector through the beam entrance aperture. Similarly, light passing through the surface enters the second collector, but the axial beam component is dumped through an opening in the second collector, while only diffracted light is collected. Preferably, two-stage light collectors are used with the first stage admitting the beam and generating a scattered or diffracted beam component, with the second stage admitting the scattered or diffracted beam component and integrating the component over a collection surface and sampling the integrated portion at a photoelectric detector. An electrical output signal from the detector may be displayed.

16 Claims, 6 Drawing Figures

DUAL COLLECTOR OPTICAL FLAW DETECTOR

CROSS REFERENCE TO RELATED APPLICATION

This application is a continuation-in-part of prior application Ser. No. 559,909, filed Dec. 9, 1983.

TECHNICAL FIELD

The invention relates to detection of fine particles and cracks, as well as holes, in sheet material or webs which are both optically reflective and transmissive, and in particular to a scanning flaw detector having light collector stages above and below an optically reflective and transmissive test surface.

BACKGROUND ART

U.S. Pat. No. 4,378,159 to Galbraith relates to a scanning laser contaminant and defect detector which uses a reflective spherical shell sector to collect light from a reflective surface under test. A photoelectric detector in the shell facing the test surface detects changes in scattering, indicative of particles which have different scattering properties than the test surface.

U.S. Pat. No. 4,243,891 to Dobler et al. teaches optical hole detection by means of light. A prism is used to uniformly illuminate a web, such as photographic film, with an optical detector on the underside of the web to detect holes in the web.

U.S. Pat. No. 4,380,032 to Pfost teaches the scanning of magnetic tape as the tape moves past an optical station looking for either reflective color marks on the tape or light transmissive holes in the tape.

One of the problems encountered in quality control of thin films, plates, wafers, foil, and other optically reflective and transmissive members is the accumulation of surface particles, as well as the occurrence of microscopic pinholes which are not intended. Such pinholes may arise from manufacturing problems or from handling. In very thin test surfaces, or surfaces having a low-to-medium optical density, an inspection beam will penetrate the test surface whether a hole is present or not. Therefore, conventional detectors will not yield meaningful data with respect to holes in the material because of the continuous presence of a detected beam through the test surface. Scientific and industrial users of these thin products often impose quality requirements which must be checked prior to using them in experiments or in manufacturing processes. For example, in semiconductor manufacturing, a substantial amount of value is added to a thin silicon wafer since the wafer is the substrate on which integrated circuits are built. Most semiconductor manufacturers have a need to know whether a wafer meets a quality specification for the starting material. Presently, a wafer or similar material can be checked for particles, but there is no single apparatus which also tests for holes, especially where the wafer is transmissive to an inspection beam.

An object of the present invention is to devise an optical instrument for simultaneously monitoring particles an optically transmissive member and checking the surface for holes.

SUMMARY OF INVENTION

The above object has been met with a flaw detector for reflective test surfaces capable of being penetrated by an inspection beam featuring a pair of light collectors, one collector above the test surface and one below the test surface. The light collectors have a reflective internal surface and geometric light-collecting properties for capturing most of the light scattered or diffracted from a test surface. These diffusely reflective collectors dump the direct beam component, i.e. the beam along the optical axis and specularly reflected from or transmitted along that axis, and capture only the scattered and diffracted beam components. The scattered beam component exists above the test surface and is due to scattering from surface particles. The diffracted beam component exists below the test surface and is due to diffraction through small holes in the surface. Both light collectors have photoelectric detectors adapted to sample scattered and diffracted beam components, produce a corresponding electrical signal, then display the signal to indicate the size and location of the flaw.

A scanning light beam is swept across the test surface in a linear pattern. After or during every line scan, the test surface is advanced so that the entire area of the test surface may be scanned. The upper light collector must have a beam entrance aperture for admitting the entirety of the scanning beam. The detector should be positioned so that no directly reflected light can enter the detector. Preferably integrating types of detectors are used for signalling the amount of light scattered or diffracted by the scanning beam. A two-stage light collector is preferably used for the collectors to preclude directly scattered or diffracted light from entering the detectors.

BEST MODE FOR CARRYING OUT THE INVENTION

Figure 1:
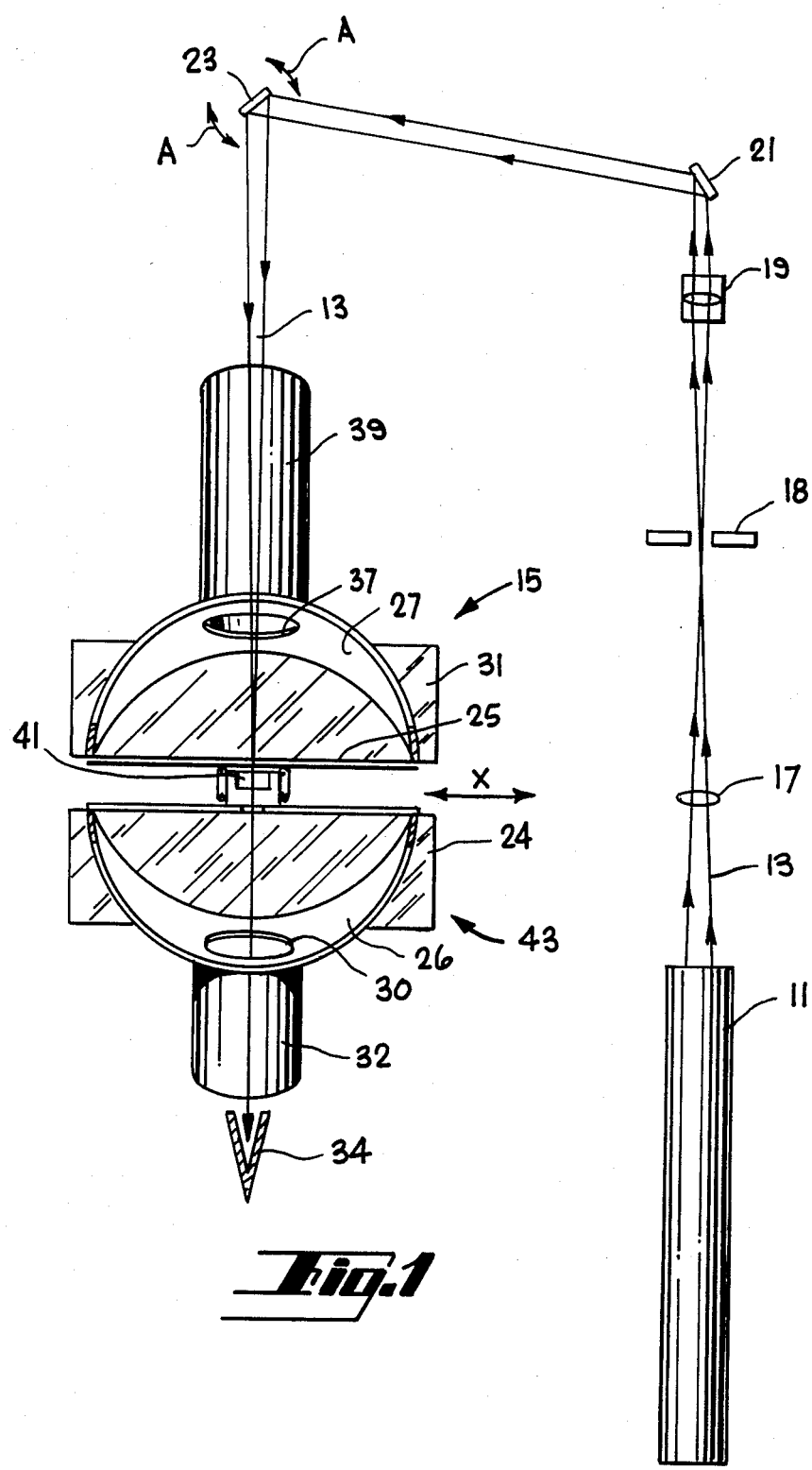
FIG. 1 is a simplified plan view of the optical flaw detector of the present invention.

With reference to FIG. 1, a low power laser 11 may be seen generating a beam 13. Laser 11 can be a helium-neon general purpose laser having an output power of a few milliwatts. A higher power laser may be preferable for greater detection capability. In some instances blue light, e.g., from a helium-cadmium laser is preferred for detection of smaller defects than with a helium-neon laser. Beam 13 is directed to focussing lens 17 and then to a beam collimating and focussing lens 19. A spacial filter 18 a short distance from lens 17 allows only the central portion of the beam to proceed. The focal length of lens 19 is approximately 14 cm. From lens 19, the beam is directed toward fixed mirror 21 and then to galvanometer mirror 23. Galvanometer mirror 23 directs light so that the focal point of the beam is at the surface 25 being scanned for defects. The surface and the defect need not be highly reflective. Reflectivity above 7 to 10% is sufficient to be detected with a low power, helium-neon laser with a sensitive detector, such as a photomultiplier tube, and the light collector of the present invention.

The present invention employs two light collectors, one above the surface being scanned and one below the surface. Both light collectors should be able to reject the direct beam component, i.e. along the optical axis after the beam impinges on the test surface. Above the test surface, this component is the specularly reflected component. Below the test surface, this component is the diffracted beam component. The light collector above the surface collects light scattered by flaws and by dirt. On the other hand the light collector below the surface collects light diffracted by cracks and holes in the surface.

With respect to the first light collector 15, above the surface 25, a shell 27, preferably spherical, faces the surface 25. The shell has a reflective coating, such as white paint, on the inside surface, facing surface 25, and an absorptive coating, such as black paint, on the outside surface. For purposes of illustration, only one-half of the shell is shown in FIG. 1. That half is shown resting on mirror surface 31 which forms half of a V-shaped trough in which the shell 27 rests. Shell 27 has a slit, or entrance aperture, through which beam 13 enters. The entrance aperture must be wide enough to accommodate the scanning beam, moving in its scanning pattern. This slit is not visible in FIG. 1. The beam passes through an exit aperture 35, visible in FIG. 2, which is opposite the beam entrance aperture.

The upper portion of the shell is termed a "crown." The inner crown surface directs light toward the mirrors, then back to the crown, and so on, until light enters the detector. Note that the shell is positioned in proximity to the surface 25 with the crown distal to the test surface and the bottom of the V-shaped trough formed by the mirror side walls in close proximity to the test surface. This is done in order that a gap between the V-shaped walls, which forms the beam exit port, be very close to the test surface. Moreover, close proximity, within a few millimeters, allows most of the scattered light from the test surface to reenter the light collector. Specularly reflected light doubles back on the beam path toward the galvanometer mirror and is lost. On the other hand, light scattered at an angle to the incident beam is collected for measurement by the detector.

The V-shaped mirror side walls have two distinct functions. First, the walls serve to optically fold the sector, allowing for a compact collector. Second, the linear gap between the base of the side walls serves as a beam exit port for a scanning beam along a linear scanning path. Each of the side walls is inclined to the vertical by an angle of 45 degrees.

A detector port 37 is defined in the shell at an acute angle with the beam entrance port relative to test surface 25. A light detector, such as a silicon cell or preferably a photomultiplier tube 39 is mounted directly over the director detector port, in a light-tight relationship therewith.

The galvanometer mirror 23 moves back and forth at a high rate, such as 800 Hz, in directions indicated by the arrows A. This causes the beam to move back and forth across test surface 25 in the X direction. Independently of this motion, surface 25 is advanced in the Z direction by a transport 41 on which the test surface is carried.

Transport 41 has a central gap which allows the downwardly directed beam to pass through. Transport 41 has a gap in its central regions allowing the beam to pass into the second light collector 43 which is below surface 25. The function of the transport is to advance the test surface incrementally a distance equal to a scanning line width as each line has been scanned. A continuously slowly moving conveyor will accomplish this result. Alternatively, a pulsed stepper motor for the transport will also work.

The second light collector 43 admits beam 13 through a gap between V-shaped mirrors. One of the mirrors 24 is seen supporting sector shell 26. The second light collector 43 is very similar to the first light collector 15. A detector port 30 is defined in shell 26 at an acute angle with the beam entrance port relative to the test surface. Photomultiplier tube 32 receives any light passing into the aperture and produces a corresponding electrical signal. The on-axis beam component passes through the shell into a beam dump 34. Thus, any beam component which is directly on-axis, for example by transmission directly through the test surface, passes through the second light collector 43. Only the off-axis, diffracted beam component, is captured by the photomultiplier. The present invention detects very small holes, compared to the beam diameter, which cause diffraction. Diffracted light is collected with second light collector 43, while rejecting non-diffracted light.

Figure 2:
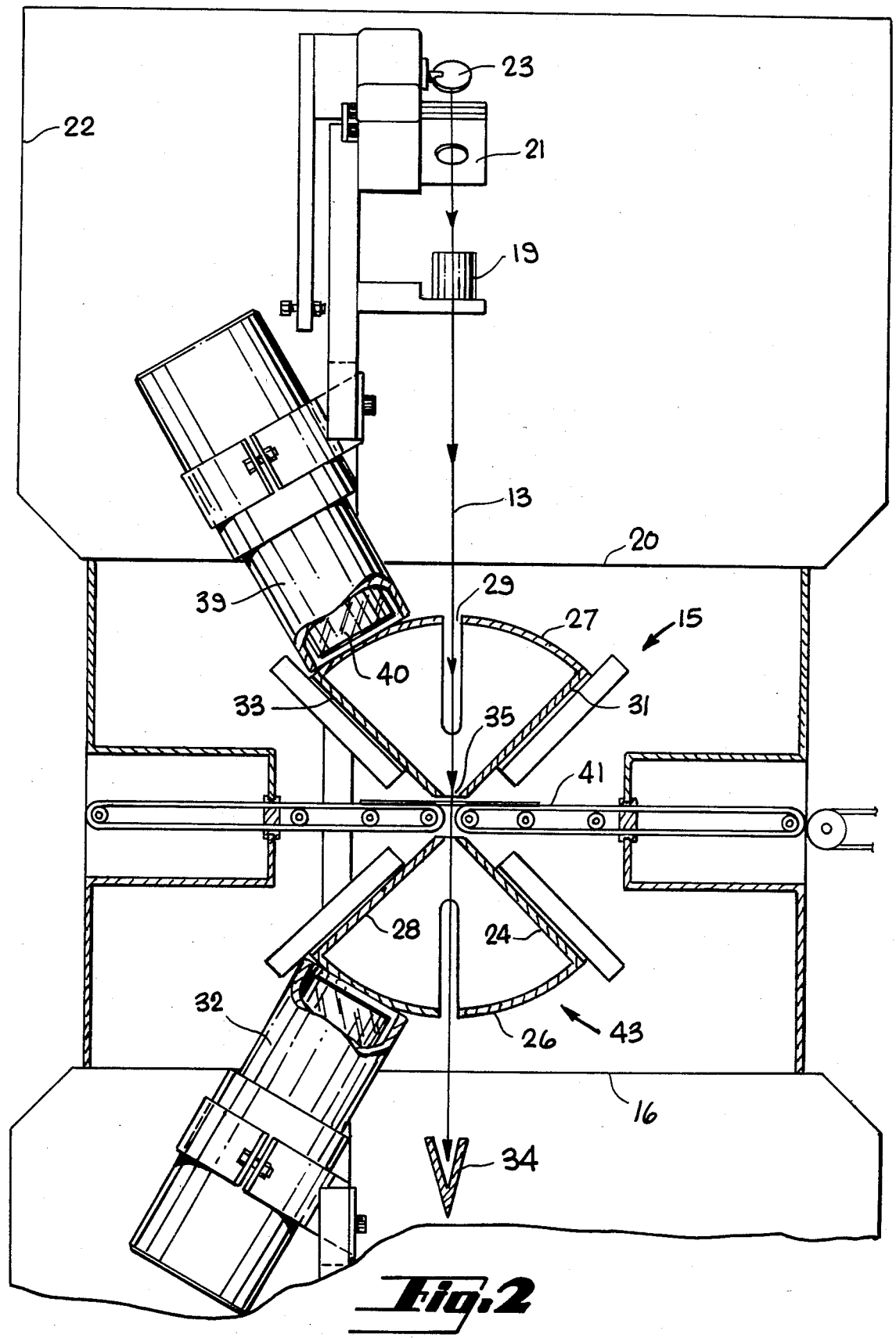
FIG. 2 is a side view of the optical flaw detector shown in FIG. 1, disposed in a housing.

FIG. 2 shows the apparatus of FIG. 1 in a partial housing formed by lower compartment 16 and upper compartment 20. An opaque shroud, 22, completely covers the top of the apparatus above the upper compartment, providing a light tight shield, totally eliminating background illumination and providing safety.

With reference to FIG. 2, light from the low power laser 11 is directed upward from lens 17 through the focussing lens 19, mirror 21 and galvanometer mirror 23, thence downward through an opening in upper compartment 20. The upper compartment provides a support for reflective article transport 41, as well as for the light collector. The light collector comprises the V-shaped flat mirrors 31 and 33, as well as the sector shell 27. An entrance aperture 29 may be seen to be immediately above an exit aperture 35 which is in a gap between the V-shaped mirror members 31 and 33.

Detector 39 may be seen making an acute angle with entrance aperture 29 relative to exit aperture 35. A test article, moving along conveyor 41 will pass immediately beneath the exit aperture 35. Any defects on the test surface or contaminants thereon will cause scattering of the beam. Upwardly scattered light will be scattered toward the reflective upper surface of shell 27 whereupon the light will be reflected to one of the mirrors 31 or 33. Eventually, light will enter the window 40 of detector 39. Preferably, detector 39 is a red-sensitive photomultiplier tube in the instance where laser 11 is a helium-neon laser.

Second light collector 43 admits beam 13 immediately below transport 41. Seen for the first time in FIG. 2, are both of the reflective V-shaped mirror members 24 and 28. Photomultiplier 32 is seen at a similar angle as photomultiplier 39 in light collector 15. Shell 26 is seen to be cradled between mirrors 24 and 28 in the same manner as shell 27 is cradled between mirrors 31 and 33. Beam 13 is shown having an on-axis component which is directed into beam dump 34. The off-axis component which is collected by photomultiplier tube 32 is not shown. However, it is the off-axis component which is significant for the purpose of indicating small pin holes, compared to the beam diameter, in test surface 35. The bands which form conveyor 41 are sufficiently spaced so that light can pass through the wafer, or other test surface, in the region above the slot in second light collector 43 if holes are present. FIG. 2 shows that by using two conveyors in series, with a slight gap between the two, clearance is provided for the beam entering the slot as it traverses the test surface.

The output of the photomultiplier tubes 39 and 32 is connected to respective comparators which also receive inputs from variable references. The variable references are signals corresponding to the amount of scattering detected from a particle having a predetermined size which may be, for example, one square micron. Any detector signal which is above the reference level causes a comparator to produce an output signal.

As previously mentioned, the transport 41 moves a surface to be tested, such as a semiconductor wafer, past the beam exit port 35. The surface slowly moves transverse to the X-direction sweep by the beam at a known rate. Beam position is known because the position of the galvanometer mirror 23 is known. The galvanometer mirror provides an X-direction address for the beam. Similarly, motion of the transport motor provides an independent Z-direction address.

The addresses are used in a random access memory to provide addresses for scattering intensities which are observed by the detectors. Three-by-three memory cells are observed using the known technique of cluster analysis. Briefly, columns of the three-by-three array cells are analyzed one at a time, left to right. The arrays are searched for aligned memory cells containing scattering data. For example, three cells in a row, each containing scattering data, would indicate the presence of a line defect. On the other hand, a single isolated memory cell containing a reading would indicate the presence of a particle. Two or three non-aligned cells containing detector data would similarly indicate one or more particles, rather than a line. The complete random access memory array of several thousand cells is analyzed in this way. At the same time, the memory array may be used to refresh a CRT or similar display device.

Light from a contaminant on a scanned surface is scattered upwardly at an angle with respect to the downwardly directed beam. Upwardly scattered light is collected at the detector with an efficiency of approximately 30%. The detector signal is independent of the scattering angle from 0 degrees to 45 degrees measured with reference to the vertical angle made by the entrance beam. The detector signals are also independent of the position of a defect or contaminant along a scanned line.

Figure 3:
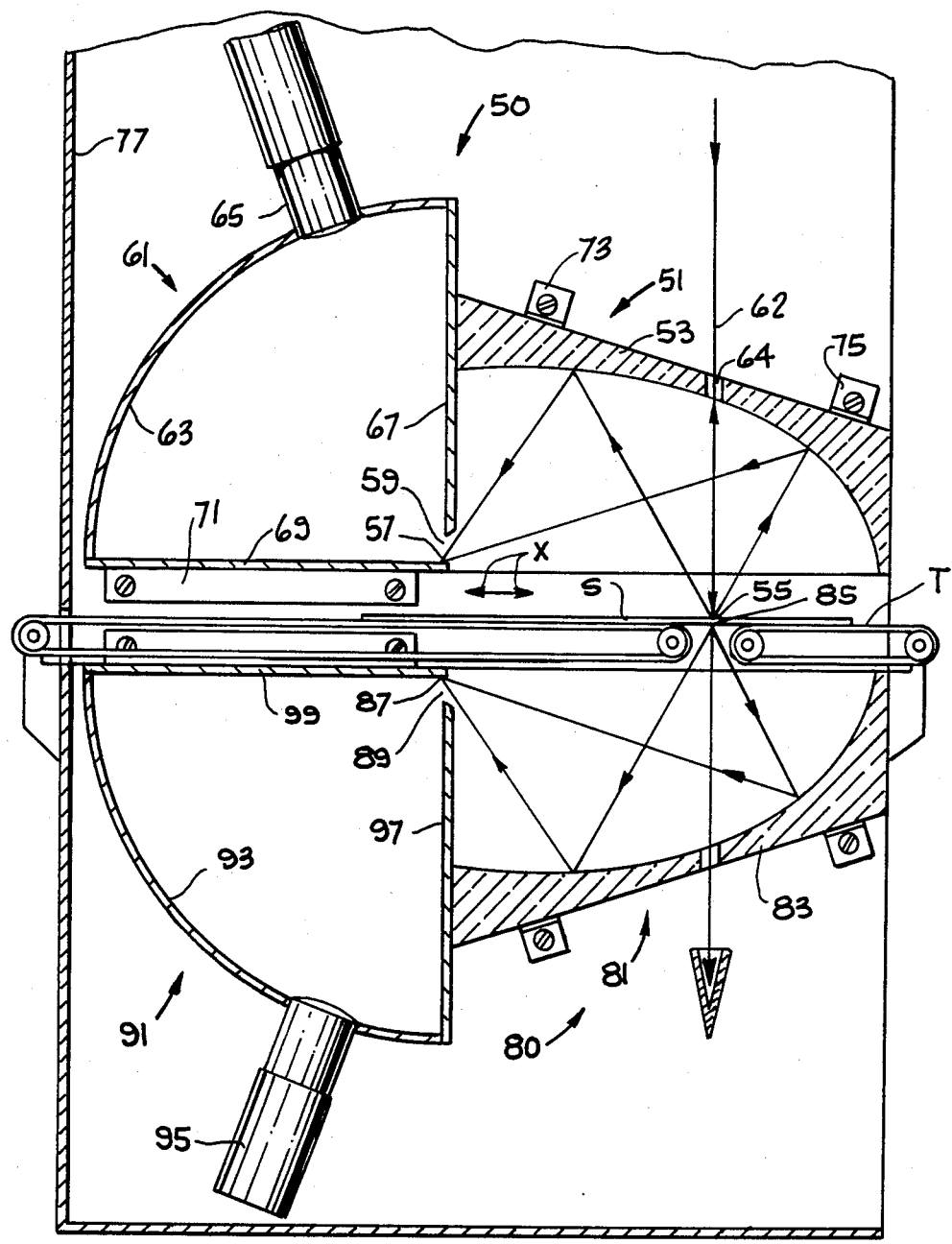
FIG. 3 is a side plan view of an alternate embodiment of an optical flaw detector of the present invention.
Figure 4:
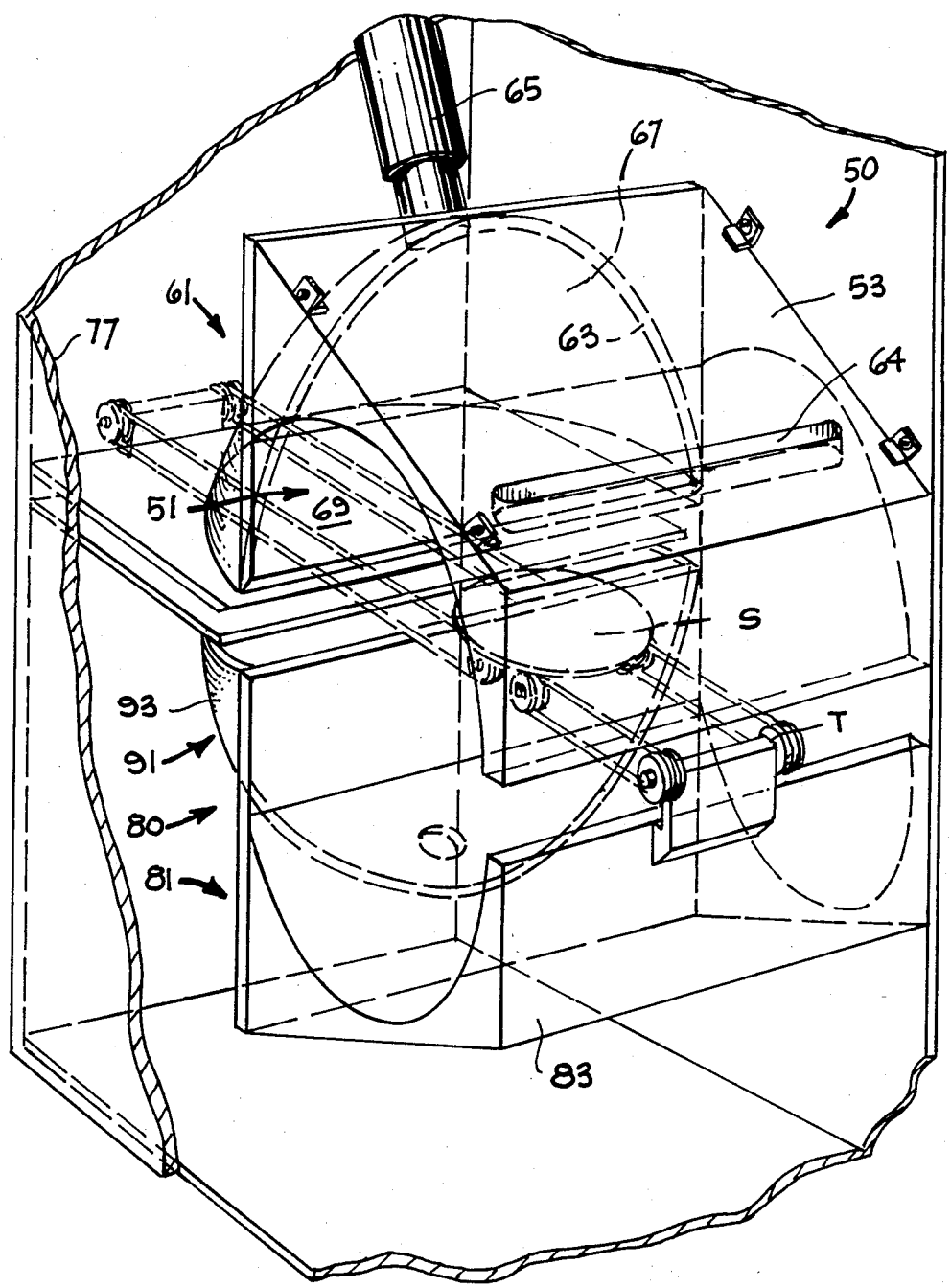
FIG. 4 is a perspective view of the device shown in FIG. 3.

With reference to FIGS. 3 and 4, two-stage light collectors are shown of the type disclosed in prior application Ser. No. 559,909, assigned to the assignee of the present invention. An advantage of using two-stage collectors arises from the fact that light scattered from other than the target surface, in a one-stage collector, may enter the detector of the one-stage collector. However, in a two-stage collector, the entrance aperture of the second stage may be made to coincide with a focal line or point of the first stage so that only desired light enters the second stage where the detector is located. Such two-stage collectors are preferred to single stage collectors, yielding increased sensitivity to contaminants.

In particular, first stage 51 of first light collector 50 includes a cylindrical mirror 53 having an elliptical cross section for the inner surface. Since an elliptical cylinder has two line foci, one focus 55 may be placed on a test surface S, while the other focus 57 may be placed at the entrance port 59 of the second stage 61. By taking advantage of the optical symmetry of these foci, light may be selectively transferred from one collector to another. Light is admitted to the first stage, as indicated by beam 63 and directed toward surface S. Light enters through beam entrance aperture 64, a crosswise slot, which permits beam 62 to scan across the full width of the test surface. A large fraction of the light scattered from the test surface at the first line focus of the cylindrical mirror 53 will be delivered to the second stage at the second line focus 57, which is the conjugate focal line of the first. Specularly reflected light on the optical axis exits via the beam entrance aperture.

The second stage 61 has a diffusely reflective spherical shell 63 cradled between V-shaped, specularly reflective side walls, resembling the light collector sector shell 27, shown in FIG. 1. However, the entrance port 59 in the second stage, at the junction of the V-shaped side walls, coincides with a conjugate focus of the first state 51. Light entering the second stage is collected at detector 65.

Mirror 53 is supported between opposed reflective side walls. The mirror has a cross sectional shape between the walls which is preferably uniform from edge to edge. An ellipse has the property of having two focal points. Correspondingly, an elliptical cylinder has two focal lines. The elliptical cylinder is laid out so that a first focal line, 55, of the ellipse will lie on the wafer surface S. All of the light collected from this focal line will be delivered to a second focal line 57 which is made to coincide with the center of the entrance aperture or port 59 of the second stage 61. The port 59, forming the entrance aperture to the second stage, is carefully controlled in width to about 3 millimeters. This is done to eliminate light from the second stage which did not originate at the first focal line 55. It is important that the target be located such that a focal line falls right on the target surface so that light which is in the vicinity of the first focal line will be delivered to the vicinity of the second focal line within a close tolerance. The entrance port of the first stage is made large enough to accommodate light from the vicinity of the first focal line, as well as from the entirety of surface S. However, the second entrance port 59 must be limited to prevent entry of unwanted light, and escape of light from the second collector.

The interior surfaces of the reflective side walls supporting mirror 53 should be flat mirrors parallel to each other and perpendicular to the axis of the elliptical cylinder. These insure that light rays scattered obliquely along the beam scan line and propagating toward the side walls will nevertheless enter the second collector after reflection from the side walls and the elliptical cylinder.

Second collector stage 61 has an internal surface 63 which is a diffusely reflective surface of a sector of a spherical shell. High reflectivity for the internal surface is desired and this is achieved by white paint or the like coating the surface. The surface 31 is cradled between two specularly reflective mirrors 67 and 69 forming side walls. The reflective side of these mirrors faces internal surface 63. The purpose of the walls is to provide support for surface 63, as well as to re-direct light back onto the surface 63 until it reaches detector 65. A gap exists at the junction of the mirror side walls 67 and 69 forming a beam entrance aperture 59 into the second stage 61. Mirrors 67 and 69 may be supported by means of brackets, such as bracket 71. Mirror surface 53 may be supported by brackets 73 and 75.

Detector 65 is positioned at a location where it will not be the recipient of directly entrant light rays. Rather, the light rays reaching detector 65 usually have been reflected between surface 63 and either or both of the reflective side walls 67 and 69 a number of times. The detector is a photomultiplier tube which converts impinging optical radiation to a corresponding electrical signal. This signal may be displayed on a CRT, or recorded, or both. The electrical signal may also be converted to a digital signal and manipulated by digital techniques.

The entire apparatus is preferably housed in a light-tight container 77 in which the various components are mounted. The container has opposed lateral walls to which the various components are connected by means of brackets.

A second two-stage light collector 80 is disposed as a mirror image of light collector 50 for capturing light diffracted by small holes in the test surface and rejecting beam component 82 which exists on the optical axis. A beam exit port 84, a crosswise slot, allows egress of the beam which projects through the test medium. Second collector 80 includes a first stage 81 identical to first stage 51 and a second stage 91, identical to second stage 61. The first stage is a mirror 83 supported between opposed reflective side walls. Once again, the mirror has a cross sectional shape which is a uniform elliptical cylinder having two focal lines. A first focal line 85 is immediately below focal line 55 on the test surface, while a second focal line 87 is in the vicinity of entrance port 89. Second stage 91 has an internal surface 93 which is a diffusely reflective surface of the sector of a spherical shell. The surface is cradled between specularly reflective mirrors 97 and 99. Light which passes through the test surface and is captured by first stage 81 is directed into second stage 91 where a portion of the light is captured by the detector 95.

In operation, beam 62 is directed through the beam entrance aperture 64 to a specularly reflecting target object, such as the surface S of a thin member. The member is mounted on a transport T to move in the direction of arrows X. The width of slit 64 is just wide enough to accommodate the scanning beam moving across the surface being scanned. Light which is scattered from the surface of the wafer thence goes to the interior wall of mirror 53 which is specularly reflective. Specularly retroreflected light from the wafer surface escapes through entrance slot 64. Most of the scattered light is captured within the first stage 51. Light diffusely reflected and scattered from the scanning line on the surface S of the wafer is directed by specular reflection to a symmetrically located line at the entrance aperture or port 59 in the second collector 61. A second stage light collector 61 is connected to the first stage for receiving light through a port 59 which extends between opposed walls. This collector has an internally diffusely reflective surface 63 with a detector at an angle so that an entering beam cannot directly enter detector 65. The surface 63 is preferably a sector of a sphere. The first and second light collector stages should be connected such that one receives light from the other. Two-stage light collector 80 collects light diffracted through member surface S in the same manner. Output signals from photodetectors 65 and 95 are separately or jointly displayed so that both particles and holes or cracks are displayed.

Figure 5:
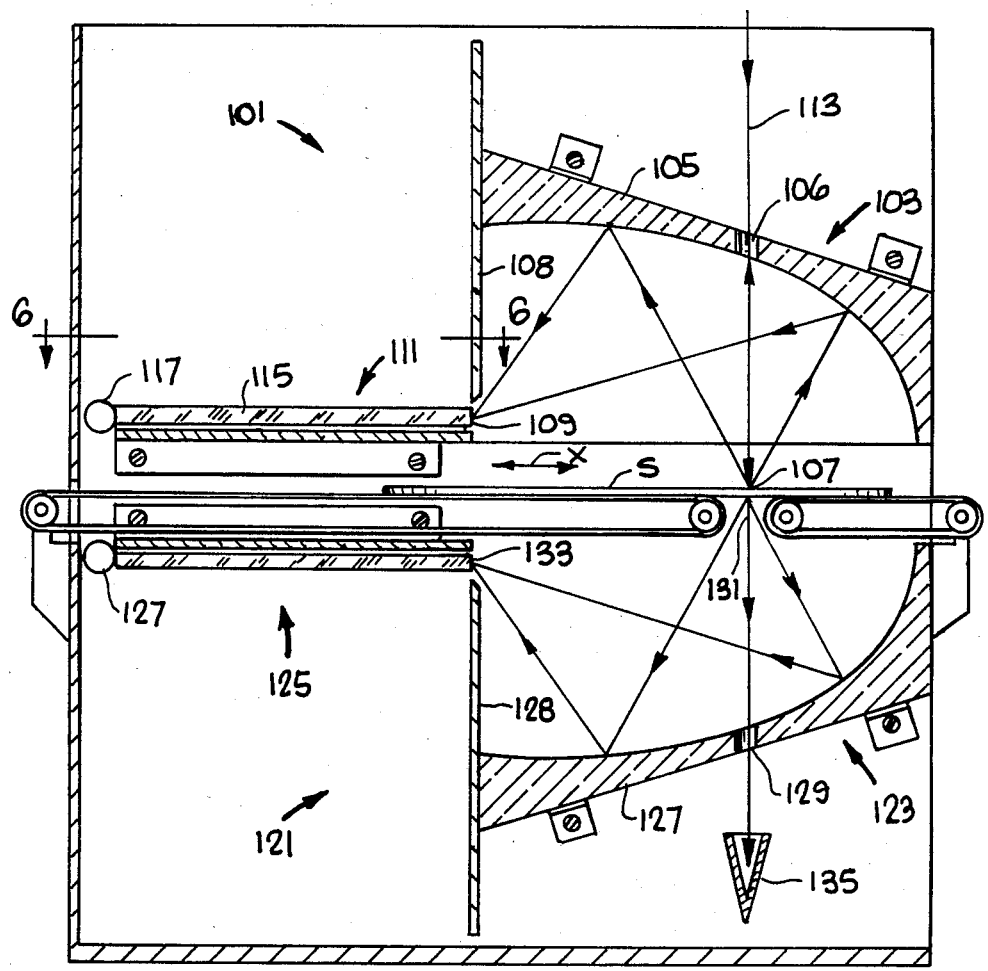
FIG. 5 is a side plan view of another alternate embodiment of an optical flaw detector of the present invention.

With reference to FIG. 5 a pair of two-stage light collectors may be seen. A first light collector 101 has a first collector stage 103 which admits beam 113. The first stage 103 is similar in construction to first stage 51 of the light collector shown in FIG. 3. This first stage includes a cylindrical mirror 105 which has an elliptical cross section for the inner surface. One elliptical focus 107 is on the test surface S, while the other elliptical focus 109 is at the entrance aperture of second collector stage 111. Both foci are lines, approximately the same length as the length of the cylindrical mirror 105. The mirror has a lengthwise slot 106 for admitting the beam so that the beam can scan across the entirety of the surface S in a raster-like pattern. Surface S may be moved in the direction indicated by arrows X. Second stage collector 111 includes a light pipe 115, which may be a fiber optic bundle, funneling light to a hollow cylindrical tube 117 having an internally diffusely reflective surface and a photomultiplier tube connected at one end for measuring incoming light. The second stage input, an end of the solid light pipe, is at an output, a focal line, of the first stage.

On the underside of surface S a similar two-stage light collector 121 is disposed. This light collector has a first stage 123 and a second stage 125. The first stage allows entry of beam 113 toward cylindrical mirror 127. The on-axis component of beam 113 is allowed to pass directly through the mirror through an aperture 129. The off-axis component of the beam is collected by the cylindrical mirror. As with mirror 105, the mirror 127 has an elliptical cross section with two-line foci. A first focus 131 of the first stage of the lower collector is coincident with first focus 107 of the upper collector or very close thereto. A second focus 133 is made to coincide with the entrance to the second light collector 125. This light collector funnels light down to a hollow tube with a photomultiplier connected thereto, similar to tube 117. Mirror 127 is partially supported by a sidewall 128, similar to sidewall 108, supporting mirror 105. Both mirror sidewalls 108 and 128 are reflective on the side facing respective first stage collectors 103 and 123 for the purpose of re-directing light which comes into these light collectors. Beam dump 135 is seen receiving the on-axis component of beam 113 which penetrates the second collector.

Figure 6:
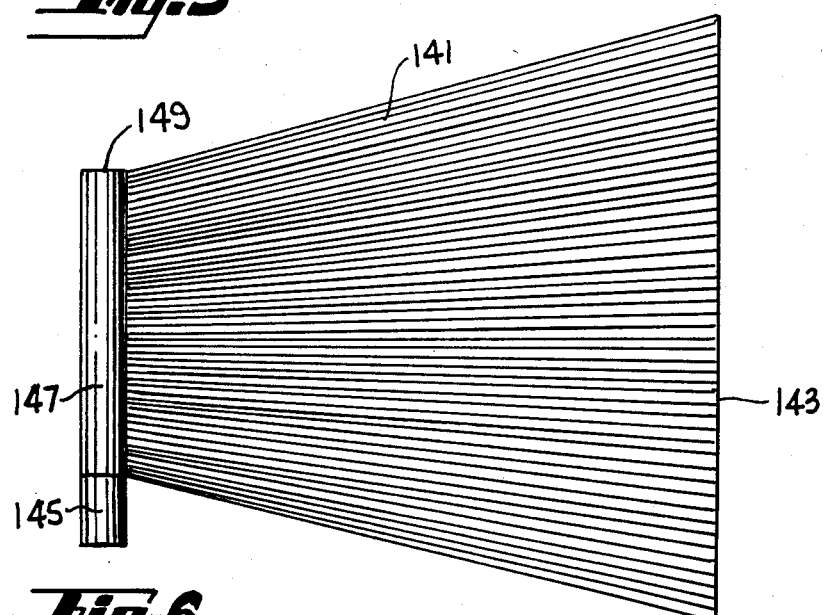
FIG. 6 is a top view of a detector and light collector taken along lines 6—6 in FIG. 5.

Operation of the two-stage light collector is the same as operation of the pair of two-stage light collectors shown and described with reference to FIGS. 3 and 4. The major difference between those two-stage light collectors and the one shown in FIG. 5 relates to the second stage which is shown in greater detail in FIG. 6. A single solid fan-shaped light pipe may be used or alternatively, a plurality of fiber optic fibers 141 may be aligned such that at one edge 143 the linear array of fibers is formed. This linear array is disposed at the entrance aperture to the second stage, along a line coinciding with an elliptical focus of the cylindrical mirror forming the first collection stage. The fiber optic bundle funnels light down toward a lengthwise slot in a tube 147 which is hollow and has an internal surface which is diffusely reflective, such as a white surface. An end 149 is closed and is also diffusely reflective. At an opposite end a photomultiplier tube 145 is disposed for receiving light which reaches the tube 147 in producing an electrical signal. Such an electrical signal will occur when the light is scattered from the test surface or is diffracted through the surface. In the first situation, particles or cracks can cause scattering, while in the second situation pin holes or cracks can cause diffraction through the test surface. The on-axis component of the beam which travels through the test surface is transmitted to a beam dump. Output electrical signals from the photodetectors may be displayed in the manner previously described for the light collector of FIG. 3.

The terms "upper" and "lower," used in referring to collector locations are intended to be understood in a relative sense, not in any absolute positive sense. As an alternative to the detector configuration of FIG. 6, the fiber optic bundle or light pipe may have its output end shaped to directly feed into a photo multiplier tube or other detector.

We claim:

1. Flaw detector apparatus for detecting particles and holes in thin test members having an optical density such that an inspection beam passes therethrough, but is partially reflected from the surface of the member, comprising,
   means for optically scanning a test surface with a beam directed along an optical axis, the beam, upon impingement with the test surface, having an axial component along said optical axis, a specularly reflected component and a scattered component above the surface and a diffracted component through any small holes in the surface,
   first light collector means disposed above said surface for admitting the beam into the first light collector means and collecting the scattered light component derived from particles on the surface while simultaneously dumping the beam component specularly reflected from the test surface, and
   second light collector means disposed below the surface for admitting the beam into the second collector means transmitted through the surface and collecting light diffracted through holes in the surface while simultaneously dumping the beam component directed along the optical axis.

2. The flaw detector of claim 1 further defined by transport means for advancing said test surface beneath said scanning beam.

3. The flaw detector of claim 1 wherein said beam scans in a linear pattern, said test surface supported by transport means for advancing said test surface beneath the scanning beam.

4. The flaw detector of claim 1 wherein said first light collector has a beam entrance aperture for admitting said scanning beam and dumping specularly reflected light from said surface and said second light collector has a beam exit aperture for dumping the axial component of said scanning beam.

5. The detector of claim 1 wherein said first and second light collectors are two-stage collectors.

6. The detector of claim 1 wherein one of said first and second light collectors comprises a sector of an internally reflective spherical shell.

7. The flaw detector of claim 1 wherein at least one of said first and second light collectors comprises an internally reflective elliptical cylinder having a first focal line on said test surface and a second focal line at an input port of an internally reflective spherical shell.

8. The flaw detector of claim 5 wherein the first stage of said first and second light collectors comprises an internally reflective cylindrical mirror having an elliptical cross section and having a first focal line on a test surface and a second focal line at an input port of an internally reflective spherical shell.

9. The flaw detector of claim 5 wherein the first stage of said first and second light collectors comprises an input port of a solid light collector feeding a hollow tube having a detector at one end.

10. The flaw detector of claim 9 wherein said solid light collector is a fiber optic bundle.

11. Flaw detector apparatus for test wafers, films and other test surfaces which can be penetrated by a light beam but are at least partially reflective of the beam comprising,
    a light source capable of generating a narrow beam,
    a support holding a test surface,
    scanning means for sweeping the beam in a path along an optical axis across the test surface,
    a first light collector above the test surface, said light collector of the integrating type having a light collection surface exposed to said test surface with an entrance aperture admitting the scanning beam as it is swept in said path, while exiting specularly reflected light, a collected light exit aperture at an angle to the beam entrance aperture having a first detector mounted therein, and
    a second light collector below the test surface with a light collection surface exposed to a region of the underside of the test surface proximate to where said beam impinges on the test surface, said second light collector admitting any portion of the scanning beam which projects through the test surface, while exiting light transmitted along the beam optical axis, a collected light exit aperture having a second detector mounted therein, whereby said first light collector collects light scattered from atop the test surface and the second light collector collects light transmitted through the test surface.

12. The apparatus of claim 11 wherein said first and second light collectors are two-stage light collectors including a first stage having means for receiving light and separating light along the optical axis from light interacting with the test surface and deflected from the optical axis and a second stage receiving and capturing said scattered light not along the optical axis.

13. The apparatus of claim 12 wherein the first stage of said first and second light collectors comprises an internally reflective cylindrical mirror having an elliptical cross section and having a first focal line on a test surface and a second focal line at an input port of an internally reflective spherical shell.

14. The flat detector of claim 12 wherein the first stage of said first and second light collectors comprises an input port of a solid light collector feeding a hollow tube having a detector at one end.

15. The flaw detector of claim 14 wherein said solid light collector is a fiber optic bundle.

16. The apparatus of claim 11 further defined by means for moving the test surface beneath said scanning beam and between said first and second light collectors for areawise scanning of the test surface.

* * * * *